United States Patent [19]

Spada et al.

[11] Patent Number: 4,859,672
[45] Date of Patent: Aug. 22, 1989

[54] PYRIDO[2,3-D]PYRIMIDINONE AND IMIDAZO[4,5-B]PYRIMIDINONE

[75] Inventors: Alfred P. Spada, Ambler; Henry F. Campbell, Lansdale; Donald E. Kuhla, Doylestown; William L. Studt, Harleysville; William C. Faith, Ambler; Bruce F. Molino, Hatfield, all of Pa.

[73] Assignee: Rorer Pharmaceutical Corporation, Fort Washington, Pa.

[21] Appl. No.: 925,008

[22] Filed: Oct. 29, 1986

[51] Int. Cl.⁴ .................... C07D 471/04; A61K 31/55
[52] U.S. Cl. .................................. 514/254; 514/258; 514/269; 514/274; 514/293; 544/238; 544/279; 544/310; 544/319; 540/502
[58] Field of Search ............... 544/238, 256, 257, 279, 544/280, 310, 319; 540/500, 501; 514/221, 248, 249, 258, 254, 269, 274, 293; 546/118

[56] References Cited

U.S. PATENT DOCUMENTS 4,026,891 5/1977 Austel .................................. 544/238
4,578,386 3/1986 Lee ...................................... 514/244
4,710,507 12/1987 Campbell ............................ 514/312

FOREIGN PATENT DOCUMENTS

84/00756 3/1984 World Int. Prop. O. .

OTHER PUBLICATIONS

Burger, Medicinal Chemistry, 2nd Ed., Interscience Publishers, Inc., N.Y.

Primary Examiner—Mark L. Berch

[57] ABSTRACT

Compounds useful for increasing cardiotonic contractility in humans or other animals and pharmaceutical compositions including these compounds are disclosed. The compounds have the general structure

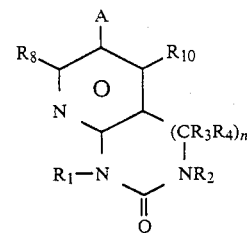

wherein:
A is

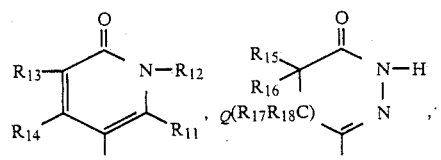

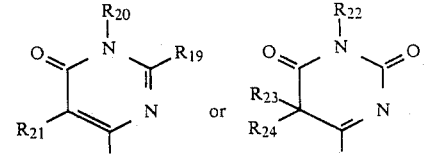

and $R_1$, $R_2$, $R_3$, $R_4$, $R_8$, $R_{10}$, $R_{11}$, $R_{12}$, $R_{14}$, $R_{15}$, $R_{16}$, $R_{17}$, $R_{18}$, $R_{19}$, $R_{20}$, $R_{21}$, $R_{22}$, $R_{23}$ and $R_{24}$ are H, lower alkyl of 1–4 carbon atoms, phenyl, substituted phenyl, phenyl lower alkyl of 1–4 carbon atoms or substituted phenyl lower alkyl of 1–4 carbon atoms;

wherein the substituted phenyl group is substituted by one or more of lower alkyl, lower alkoxy, amino, lower alkyl amino, lower alkyl mercapto, hydroxy, hydroxy lower alkyl, acetoxy, benzyloxy, phenoxy, lower alkyl sulfinyl or lower alkyl sulfonyl;

$R_{13}$ is H, lower alkyl of 1–4 carbon atoms, alkoxy lower alkyl of 1–4 carbon atoms, hydroxy lower alkyl of 1–5 carbon atoms, amino, carbamoyl, cyano, lower alkyl carbamoyl of 1–4 carbon atoms, formyl, amino lower alkyl of 1–4 carbon atoms, carboxy, carbalkoxy, or tetrazolyl;

$R_3$ and $R_4$ together may form =O;
$R_{16}$ and $R_{17}$ together may form a carbon-carbon bond;
n is 0 or 1; and
Q is 0 or 1.

17 Claims, No Drawings

PYRIDO[2,3-D]PYRIMIDINONE AND IMIDAZO[4,5-B]PYRIMIDINONE

FIELD OF THE INVENTION

This invention relates to novel compounds which possess useful cardiotonic properties. This invention relates also to the uses of said compounds including methods for increasing cardiac contractility, which can be used, for example, for the treatment of congestive heart failure, pharmaceutical compositions including the same and methods for the preparation thereof.

BACKGROUND OF THE INVENTION congestive heart failure is a life-threatening condition in which myocardial contractility is depressed so that the heart is unable to pump adequate amounts of blood to meet the body's metabolic needs. The leading causes for heart failure are believed to be an inadequate oxygen supply to the heart muscle or cardiomyopathy, a disorder of abnormality in the heart muscle tissue. As cardiac output decreases, other neurological mechanisms are activated, causing arterial and venous constriction, the redistribution of tissue blood flow and an increase in circulatory blood volume. As the condition worsens, the patient experiences edema, increased heart size, increased myocardial wall tension, and eventually the heart stops pumping.

Drugs which increase the tone of the heart muscle are described as having positive inotropic activity and are characterized as cardiotonic agents. Digitalis glycosides have long been used to increase myocardial contractility and reverse the detrimental changes seen in congestive heart failure. More recently, dopamine, dobutamine, amrinone and milrinone have been used to provide necessary inotropic support for the failing heart.

Cardiotonic agents which are described as having positive inotropic activity include the 5-pyridyl substituted pyridones disclosed in U.S. Pat. Nos. 4,004,012; 4,072,746; 4,107,315; 4,137,233; 4,199,586; 4,271,168; and 4,107,315; in GB No. 20706006A; and in PCT published Appl. No. PCT/CH81/00023 which corresponds to Great Britian No. 2,070,606. Other cardiotonic drugs include the diazacyclic substituted carbostyril compounds disclosed in U.S. Pat. Nos. 4,414,390 and 4,415,572, cardiotonic pyridyl substituted carbostyril compounds disclosed in EPO application Ser. No. 84308925.1, and the 5-phenyl-thiazole compounds disclosed in U.S. Pat. No. 4,418,070.

Cardiotonic bicyclic heteroaryl-5-substituted pyridyl compounds are disclosed in PCT published application Ser. No. PCT/US83/01285 which corresponds to U.S. Ser. No. 06/410,646, now abandoned; and, cardiotonic diazaheterocyclic-5-substituted pyridyl compounds are disclosed in U.S. Pat. Nos. 4,432,979, 4,514,400 and 4,539,321. Each of the aforementioned is assigned to the same assignee as the present application.

SUMMARY OF THE INVENTION

The present invention relates to compounds according to the structure

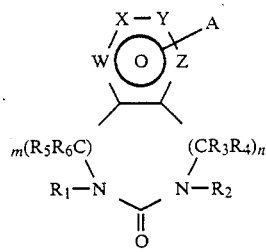

wherein A is

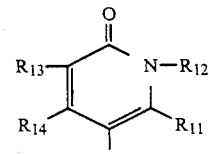

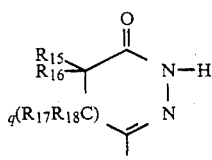

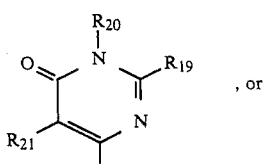

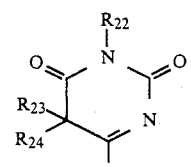

or a pharmaceutically acceptable salt thereof, wherein the other terms are defined herein.

It has been found that compounds within the scope of the present invention possess surprising and unexpected positive inotropic activity.

This invention relates also to pharmaceutical compositions which are effective in increasing cardiac contractility in humans and other animals and which are useful for the treatment of cardiac failure such as congestive heart failure.

DETAILED DESCRIPTION

The broad scope of the invention includes compounds structure I wherein
  W is N or $CR_7$,
  X is N or $CR_8$,
  Y is N or $CR_9$,
  Z is N or $CR_{10}$
with the proviso that at least one and no more than two of W, X, Y and Z are N. The N-oxide derivatives of W, X, Y and Z are included within the invention.
  m, n and Q are independently 0 or 1.
  $R_1$, $R_2$, $R_3$, $R_4$, $R_5$, $R_6$, $R_{11}$, $R_{12}$, $R_{14}$, $R_{15}$, $R_{16}$, $R_{17}$, $R_{18}$, $R_{19}$, $R_{20}$, $R_{21}$, $R_{23}$, and $R_{24}$ are independently hydrogen, lower alkyl, aryl or aralkyl.

$R_{16}$, and $R_{17}$ may together form a carbon-carbon double bond.

$R_3$ and $R_4$ together can form =O.

$R_5$ and $R_6$ together can form =O.

$R_7$, $R_8$ and $R_9$ and $R_{10}$ independently are hydrogen, lower alkyl, aryl, aralkyl or form a chemical bond with A.

$R_{13}$ is hydrogen, lower alkyl, alkoxyalkyl, cyano, amino, carbamoyl, alkyl carbamoyl, formyl, aminoalkyl, carboxy, carbalkoxy, or tetrazole.

Preferred are compounds of the structure

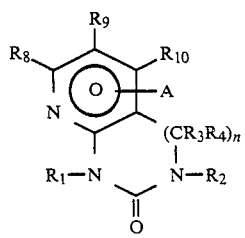

More preferred are compounds wherein $R_9$ forms a chemical bond with A, and A is of structure II or III.

Most preferred are compounds of the structure

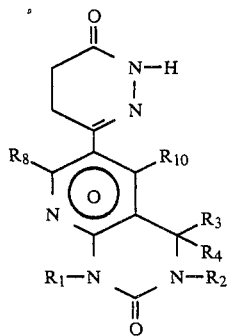

wherein $R_1$, $R_2$, $R_4$, $R_8$ and $R_{10}$ are independently hydrogen or lower alkyl, $R_3$ is hydrogen, or $R_3$ and $R_4$ together form =O.

The most preferred embodiment of the present invention comprise the compound 6-[6'(4', 5'-Dihydro-3(2H)-3-oxopyridazinyl)]-3,4-dihydro-1-methylpyrido-[2,3-d]pyrimidin-2(1H)-one or a pharmaceutically acceptable salt thereof.

Certain of the compounds encompassed within the scope of the present invention, and particularly, compounds of the above formula, may exist in enolic or tautomeric forms. All of such forms are considered as being included within the scope of this invention.

The compounds of this invention may be useful in the form of the free base, in the form of salts, and as a hydrate. All of such forms are considered as being within the scope of this invention.

Acid addition salts are a convenient form for use. In practice, use of the salt form inherently amounts to use of the base form. Acids which can be used to prepare the acid addition salts include preferably those which produce when combined with the free base, pharmaceutically acceptable salts, that is, salts whose anions are non-toxic to the animal organism in pharmaceutical doses of the salts, so that the beneficial cardiotonic properties inherent in the free base are not vitiated by side effects ascribable to the anions. Although pharmaceutically acceptable salts of said basic compound are preferred, all acid addition salts are useful as sources of the free base form even if the particular salt per se is desired only as an intermediate product as, for example, when the salt is formed only for puposes of purification and identification, or when it is used as an intermediate in preparing a pharmaceutically acceptable salt by ion exchange procedures.

Examples of pharmaceutically acceptable salts within the scope of the invention are those derived from the following acids: mineral acids such as hydrochloric acid, sulfuric acid, phosphoric acid and sulfamic acid; and organic acids such as acetic acid, citric acid, lactic acid, tartaric acid, malonic acid, methanesulfonic acid, ethanesulfonic acid, benzenesulfonic acid, p-toluenesulfonic acid, cyclohexylsulfamic acid, quinic acid, and the like. The corresponding acid addition salts comprise the following: hydrochloride, sulfate, phosphate, sulfamate, acetate, citrate, lactate, tartrate, malonate, methanesulfonate, ethanesulfonate, benzenesulfonate, p-toluenesulfonate, cyclohexylsulfamate and quinate, respectively.

The acid addition salts of the compounds of this invention can be prepared either by dissolving the free base in an aqueous or aqueous-alcohol solution or other suitable solvent(s) containing the appropriate acid and isolating the salt by evaporating the solution, or by reacting the free base and acid in an organic solvent, in which case the salt separates directly or can be obtained by concentration of the solution.

As employed above and throughout the disclosure, the following terms, unless otherwise indicated, shall be understood to have the following meanings:

"Alkyl" means a saturated aliphatic hydrocarbon which may be either straight- or branched-chained containing from about one to about six carbon atoms.

"Lower alkyl" means an alkyl group as above, having one to about four carbon atoms.

"Alkyl carbamoyl" means a carbamoyl group substituted by one or two alkyl groups. Preferred groups are the lower alkyl carbamoyl groups.

"Alkoxy" means an alkyl oxy group in which "alkyl" is as previously described. Lower alkoxy groups are preferred and include methoxy, ethoxy, n-propoxy, i-propoxy, sec-propoxy, n-butoxy among others.

"Alkoxyalkyl" means an alkyl group as previously described substituted by an alkoxy group as previously described.

"Aminoalkyl" means —$RNH_2$ where —R is alkyl of one to about six carbon atoms. The preferred groups are the lower aminoalkyl groups which means amino groups substituted with alkyl groups of one to about four carbon atoms. The most preferred aminoalkyl group is aminomethyl.

"Aryl" means an aromatic hydrocarbon radical. The preferred aryl groups are phenyl and substituted phenyl.

"Aralkyl" means an alkyl group substituted by an aryl radical. The preferred aralkyl groups are lower alkyl groups substituted by phenyl or substituted phenyl.

"Substituted phenyl" means a phenyl group substituted by one or more of lower alkyl, lower alkoxy, amino, lower alkyl amino, lower alkyl mercapto, hydroxy, hydroxy lower alkyl, acetoxy, benzyloxy, phenoxy, lower alkyl sulfinyl or lower alkyl sulfonyl.

The compounds of this invention can be normally administered orally or parenterally, in the treatment of cardiac disorders such as heart failure in humans or other mammals.

The compounds of this invention, preferably in the form of a salt, may be formulated for administration in any convenient way, and the invention includes within its scope pharmaceutical compositions containing at least one compound according to the invention adapted for use in human or veterinary medicine. Such compositions may be formulated in a conventional manner using one or more pharmaceutically acceptable carriers or excipients. Suitable carriers include diluents or fillers, sterile aqueous media and various non-toxic organic solvents. The compositions may be formulated in the form of tablets, capsules, lozenges, trochees, hard candies, powders, aqueous suspensions, or solutions, injectable solutions, elixirs, syrups and the like and may contain one or more agents selected from the group including sweetening agents, flavoring agents, coloring agents and preserving agents, in order to provide a pharmaceutically acceptable preparation.

The particular carrier and the ratio of inotropic active compound to carrier are determined by the solubility and chemical properties of the compounds, the particular mode of adminstration and standard pharmaceutical practice. For example, excipients such as lactose, sodium citrate, calcium carbonate and dicalcium phosphate and various disintegrants such as starch, alginic acid and certain complex silicates, together with lubricating agents such as magnesium stearate, sodium lauryl sulphate and talc, can be used in producing tablets. For a capsule form, lactose an high molecular weight polyethylene glycols are among the preferred pharmaceutically acceptable carriers.

Where aqueous suspensions for oral use are formulated, the carrier can be emulsifying or suspending agents. Diluents such as ethanol, propylene glycol, glycerin and chloroform and their combinations can be employed as well as other materials.

For parenteral administration, solutions or suspensions of these compounds in aqueous alcoholic media or in sesame or peanut oil or aqueous solutions of the soluble pharamceutically acceptable sales described herein can be employed. Solutions of the salts of these compounds are especially suited for intramuscular and subcutaneous injection purposes. The aqueous compositions, including solutions of the salts dissolved in pure distilled water are also useful for intravenous injection purposes, provided that their pH is properly adjusted, suitably buffered, made isotonic with sufficient saline or glucose and sterilized by heating or by microfiltration. Certain compositions useful for intravenous injection or infusion may be prepared using the solid form of the active compound of the present invention. The solid compound may be suspended in propylene glycol, or a polyethylene glycol ether such as PEG 200, using a sonicator and the resulting mixture combined with aqueous media.

The dosage regimen in carrying out the methods of this invention is that which insures maximum therapeutic response until improvement is obtained and thereafter the minimum effective level which gives relief. Thus, in general, the dosages are those that are therapeutically effective in increasing the contractile force of the heart or in the treatment of cardiac failure. Exemplary of such doses are a oral dose which may be between about 0.001 mg/kg and about 30 mg/kg (preferably in the range of 0.001 to about 10 mg/kg), and the i.v. dose of about 0.001 to about 10 mg/kg (preferably in the range of 0.001 to about 3 mg/kg). It should be borne in mind that, in selecting the appropriate dosage in any specific case, consideration must be given to the patient's weight, general health, age and other factors which may influence response to the drug. The drug may be administered as frequently as is necessary to achieve and sustain the desired therapeutic response. Some patients may respond quickly to a relatively large or small dose and require little or no maintenance dosage. On the other hand, other patients may require sustained dosing from about one to about four times a day depending on the physiological needs of the particular patient. It is anticipated that many patients will require no more than about one to about two doses daily.

It is also anticipated that the present invention would be useful as an injectable dosage form which may be administered in an emergency to a patient suffering from acute cardiac failure. Such treatment may be followed by intravenous infusion of the active compound and the amount of compound infused into such patient should be effective to achieve and maintain the desired therapeutic response.

Compounds within the scope of the present invention may be prepared as shown in the following examples.

EXAMPLES

EXAMPLE 1

A. Preparation of 2-(methylamino)-nicotinonitrile:

A solution of 2-chloronicotinonitrile (97.82 g, 706 mmol) in 40% aqueous methylamine (706 ml) was heated to reflux for 1.5 hour. The excess methylamine was evaporated off and the resulting solids filtered and washed with water (250 mL). The crude product was dissolved in boiling water (1.4 l) and treated with charcoal and filtered through Celite. The aqueous filtrate was cooled to room temperature. After 10 hours the crystalline solid was collected, washed with water and dried to leave 71.10 g of 2-(methylamino)-nicotinonitrile (mp. 86–88 degrees C.). A sample was further purified by sublimation (100 degrees C. at 0.025 mm) mp. (87–88 degrees C.).

Calculated C, 63.14; H, 5.30; N, 31,56; Found C, 63.21; H, 5.27; N, 32.36.

B. Preparation of 3-(aminomethyl)-2-methylaminopyridine:

Borane/THF complex (1.44 mol) as a 1M solution in tetrahydrofuran was added, dropwise, to a solution of 2-(methylamino)-nicotinonitrile (63.9 g, 480 mmol) in tetrahydrofuran (480 mL). This mixture was stirred at room temperature for 1 hour then heated to reflux for 3 hours. The reaction mixture was quenched by dropwise addition of methanol (136 mL, 3.36 mol) followed by 6M HCl (80 mol, 480 mmol) and 10% HCl (400 mL). The phases were separated and the organic phase washed with brine (2×480 mL). The aqueous phase was made alkaline with 50% aqueous NaOH (250 g). The aqueous phase was extracted with dichloromethane (2×480 mL) and the organic extracts dried over Na$_2$SO$_4$. Concentration in vacuo gave 44.85 g of 3-(aminomethyl)-2-methylaminopyridine as a pale yellow oil.

C. Preparation of 3,4-dihydro-1-methylpyrido[2,3-d]-pyrmidin-2(1H)-one:

1,1' Carboxyldimidazole (48.2 g, 297 mmol) was added to a solution of 3-(aminomethyl)-2-methylaminopyridine (39.79 g, 290 mmol). The resulting mixture was heated to reflux for 6 hours. This mixture was concentrated in vacuo and the resulting white solid was dissolved in dichloromethane (580 mL) and stirred with 10% NaOH (290 mL) for 0.75 hours. The phases were separated and the aqueous phase washed with chloroform (1×580 mL). The combined organic phases were washed with 10% NaOH (290 mL) dried over $Na_2SO_4$ and concentrated in vacuo. The resulting solid was recrystallized from toluene and dried under reduced pressure (200 mm) at 75 degrees C. for 1 hour to leave 39.38 g of 3,4-dihydro-1-methylpyrido[2,3-d]pyrimidin-2(1H)-one as a white crystalline solid (mp 140-3 degrees C.).

Calculated % C, 58.89; H, 5.56; N, 25.75; Found % C, 58.47; H, 5.58; N, 25.92.

D. Preparation of 6-bromo-3,4-dihydro-1-methyl-pyrido-[2,3d]pyrimidin-2-(1H)-one:

A solution of N-bromosuccinimide (34.47 g 193.65 mmol) in N,N-dimethylformamide (DMF) was added, over 0.75 h, to a stirred suspension of 3,4-dihydro-1-methylpyrido-[2,3-d]pyrimidin-2(H)-one (31.60 g, 193.65 mmol) in DMF (316 mL) at −45 degrees C. This mixture was maintained at −40 degrees C. for 2.5 hours, and diluted with water (632 mL) stirred at room temperature for 1 hour. The resulting crystalline white solid was filtered, washed with water (632 mL) dried with suction then in vacuo (approximately 200 mm) at 75 degrees C. for 15 hours to leave 35.90 g of 6-bromo-3,4-dihydro-1-methylpyrido[2,3-d]pyrimidin-2(1H)-one as white crystalline solid (mp 216–17 degrees C.).

Calculated % C, 39.69; H, 3.33; N, 17.36; Br, 33.01; Found % C, 39.55; H, 3.38; N, 17.20; Br, 32.73, 32.62.

E. Preparation of 6-bromo-1-methyl-1-ethoxy-4(1H)-pyrido[2,3-d]pyrimidine:

Triethyloxonium tetrafloroborate (87 mmol), as a 1M solution in dichloromethane was added dropwise to a mechanically stirred suspension of 6-bromo-3,4-dihydro-1-methylpyrido[2,3d]pyrimidin-2(1H)-one (7.0 g, 28.9 mmol) in dichloromethane (350 mL) containing $K_2CO_3$(20 g, 144.5 mmol). This mixture was maintained for 3 days under nitrogen quenched by dropwise addition of saturated aqueous $NaHCO_3$(50 mL), diluted with additional dichloromethane (150 mL). The phases were separated and the aqueous phase washed with dichloromethane (100 mL). The combined extracts were filtered through a cotton plug and concentrated in vacuo to leave 8.7 g of an off white solid which was purified by column chromatography (chloroform:methanol 95:5) to leave 6.8 g of 6-bromo-1-methyl-2-ethoxy-4(1H)pyrido[(2,3-d)]pyrimidine.

F. Preparation of 6-(trimethylstannyl)-1-methyl-2-ethoxy-4(H)pyrido[2,3-d]pyrimidine:

t-Butyllithium (50.0 mmol) was added as a solution in pentane to a mixture of 6-bromo-1-methyl-2-ethoxy-4(H)pyrido[2,3-d]pyrimidine(4.5 g, 16.6 mmol), cooled to −78 degrees C., tetrahydrofuran (130 mL). After 1.3 h at −78 degrees C. a solution of trimethylstannyl chloride (9.6 g, 50.0 mmol) in tetrahydrofuran (30 mL) was added. The resulting yellow solution was maintained at −78 degrees C. for 3.5 hours, quenched with saturated $NH_4$+Cl− (100 mL), diluted with ethyl acetate (100 mL) and extracted with ethyl acetate (2×100 mL). The combined organic extracts were dried over $Na_2SO_4$ and concentrated in vacuo to leave 11.8 g of 6-(trimethyl-stannyl-1-methyl-2-ethoxy-4(H)-pyrido[2,3-d]pyrimidine. Purification was achieved by column chromatography (dichloromethane:methanol 95:5) to leave 6.3 g of red oil.

G. Preparation of 6-(trimethylstannyl)-3,4-dihydro-1-methyl-3-acetylpyrido[2,3-d]pyrimidin-2(1H)-one:

A solution of 6-(trimethylstannyl)-1-methyl-2-ethoxy-4(H)-pyrido[2,3-d]pyrimidine(1.3 g, 3.7 mmol), in anhydrous dichloromethane (15 mL) containing acetyl chloride (886 mg, 11.3 mmol) was maintained under nitrogen for 0.5 hours. This mixture was diluted with dichloromethane (50 mL), extracted with ⅓ sat. $NaHCO_3$ (2×20 mL), filtered through cotton and concentrated in vacuo to leave 1.6 g of 6-(trimethylstannyl)-3,4-dihydro-1-methyl-3-acetylpyrido[2,3-d]pyrimidin-2(1H)one as a red oil. This material was of sufficient purity to use without further purification. A pure sample of 6-(trimethylstannyl)-3,4-dihydro-1-methyl-3-acetylpyrido[2,3-d]pyrimidin-2(1H)-one can be obtained as a clear, colorless oil by column chromatography.

H. Preparation of 6-[1'-(3'-carbomethoxy-1'-oxypropyl)]-3,4-dihydro-1-methyl-3-acetypyrido[2,3-d]pyrimidin-2(1H)-one:

A solution of 6-(trimethylstannyl)-3,4-dihydro-1-methyl-3-acetylpyrido[2,3-d]pyrimidin-2(1H)-one(2.1 g,5.4 mmol) in benzene (60 mL) containing $PdCl_2$ $(PPh_3)_2$ (65 mg, 0.13 mmol) was heated to reflux, under nitrogen, for 3 hours. The reaction mixture was cooled, extracted with ⅓ sat $NaHCO_3$ (3×15 mL), dried over $Na_2SO_4$ and concentrated in vacuo to leave 2.3 g of a tan colored solid.

The crude produce was purified by recrystallization from ethyl acetate and petroleum ether to afford a total of 1.4 g of 6-[1'-(13'-carbomethoxy-1'-oxypropyl)]-3,4-dihydro-1-methyl-3-acetylpyrido[2,3-d]pyrimidin-2(1H)-one as a tan solid (mp 146-9 degrees). An analytical sample of this material was obtained by thick layer chromatography (dichloromethane:methanol (9:1)) to afford a white solid (mp. 148-50 degrees C.).

Calculated (¼ hydrate): %C, 55.63; H, 5.44; N, 12.97; Found: %C, 55.30; H, 5.52; N, 12.85.

I. Preparation of 6-[6'-(4',5'-Dihydro-3(2H)-3-oxopyridazinyl)]-3,4-dihydro-1-methylpyrido[2,3-d]pyrimidin-2(1H)-one:

A suspension of 6-[1'-(3'-carbomethoxy-1'-oxypropyl)]-3,4-dihydro-1-methyl-3-acetylpyrido[2,3-d]pyrimidin-2(1H)-one(1.53 g, 4.8 mmol) in absolute ehtanol (55 mL) containing hydrazine hydrate (2.4 g, 47.9 mmol) was heated to reflux for 8 hours.

The resulting mixture was cooled to 0 degrees C., filtered and washed with water (5×20 mL). The filtrate was dissolved in 3M HCl (80 mL) and filtered. The pH of the aqueous solution was adjusted to 6 with 25% aqueous NaOH. The resulting solids were filtered, washed with water (5×20 mL) and dried at 70 degrees C. in vacuo (200 mm) to leave 1.0 g of 6-[6'-(4,5'-dihydro-3(2H)-3-oxo-pyridazinyl)]-3,4-dihydro-1-methyl-pyrido-[2,3-d]pyrimidin-2(1H)-one as a grey solid, (mp 302-310 degrees C. dec). Analysis:

Calculated (¼ hydrate) %C, 54.73; H, 4.99; N, 26.59; Found %C, 54.56; H, 5.20; N, 26.34

EXAMPLE 2

A. Preparation of 6-bromo-3,4-dihydro-1,3-dimethyl-pyrido[2,3-d]pyrmidin-2(1H)-one:

Lithium hexamethyldisilane (22.7 mmol), as a 1M solution in tetrahydrofuran, was added to stirred suspension of 6-bromo-3,4-hydro-1-methylpyrido[2,3-d]-pyrimidin-2(1H)-one, (5.0 g, 20.6 mmol) in tetrahydrofuran (50 mL). The resulting solution was maintained under an atmosphere of nitrogen for 0.5 hour. This mixture was treated with dimethylsulfate (2.87 g, 22.7 mmol) and maintained at ambient temperature, under nitrogen, for 6 hours. To this reaction mixture was added aqueous $NH_4^+Cl^-$ (15 mL) and ethyl acetate (50 mL). The phases were separared and the aqueous phase was washed with another portion of ethyl acetate (50 mL). The combined organic extracts were dried over $Na_2SO_4$ and concentrated in vacuo leaving 5.3 g of a white solid. Purification by column chromatography ($SiO_2$, $CH_2Cl_2$:$CH_3OH$, 95;5) afforded 4.26 g (81%) of 6-bromo-3,4-dihydro-1,3-dimethylpyrido[2,3-d]-pyrimidin-2(1H)-one, (mp. 119–20 degrees C.).

Calculated: %C, 42.21; H, 3.93; N, 16.41; Br, 31.20; Found %C, 41.97; H,3.83; N, 16.35; Br, 30.9; %C, 42.04; H,3.76; N, 16.31.

B. Preparation of 6-(2'-oxypropyl)-3,4-dihydro-1,4-dihydro-1,3-dimethylpyrido[2,3-d]pyrimidin-2(1H)-one:

To a solution of 6-bromo-3,4-dihydro-1,3-dimethylpyrido[2,3-d]pyrimidin -2(1H)-one(3 g, 11.7 mmol) in benzene (50 mL) was added tri-O-tolylphosphine (357 mg, 1.17 mmol), palladium acetate (131 mg, 0.58 mmol), isopropenylacetate (1.78, 17.6 mmol) and tributyltin methoxide (5.6 g, 17.6 mmol). The reaction vessel was sealed and heated to 75 degrees C. for 18 hours. The crude reaction mixture was treated with saturated aqueous $NH_4^+Cl^{31}$ (50 mL) and diluted with ethylacetate (50 mL). The phases were separated and the aqueous phase washed with ethyl acetate (3×50 mL). The combined organic extracts were filtered, dried over $Na_2SO_4$ and concentrated in vacuo to leave a green oil. This material was dissolved in dichloromethane (200 mL) and extracted with 3M HCl (2×200 mL). The aqueous extracts were treated with 4M NaOH and adjusted to pH 11. This aqueous mixture was extracted with ethyl acetate (3×200 mL). and the combined organic extracts dried over $Na_2SO_4$ and concentrated in vacuo to leave 2.0 g (74%) of 6-(2'oxypropyl)-3,4-dihydro-1,3-dimethylpyrido[2,3-d]pyrimidin-2(1H)-one as a pale yellow solid.

C. Preparation of 6-[1'-N,N-dimethylamino-3'-oxobuten-2'-yl]-3,4-dihydro-1,3-dimethylpyrido-[2,3-d]pyrimidin-2(1H)-one:

To a solution of 6-(2'-oxypropyl)-3,4-dihydro-1,3-dimethylpyrido[2,3-d]pyrimidin-2(1H)-one (1.1 g, 4.71 mmol) in N,N-dimethylformamide dimethylacetal (10 mL) was added pyridine (1 mL). This mixture was heated to 70 degrees C. under an atmosphere of nitrogen for 4 hours. This mixture was concentrated in vacuo to leave 1.3 g of a dark solid. The crude product was purified by column chromatography ($SiO_2$, $CH_2Cl_2$:$CH_3OH$, 95:5) to leave 530 mg (39%) of 6-[1'N,N-dimethylamino-3'-oxobuten-2'yl]-3,4-dihydro-1,3-dimethylpyrido[2,3-d]pyrimidin-2(1H)-one as a pale yellow solid (mp. 159–63 degrees C.).

D. Preparation of 6-[3'-cyano-6'-methyl-2'-oxo-(1H)-pyridin-5'-yl]-3,4-dihydro-1,3-dimethylpyrido[2,3-d]-pyrimidin-2(1H)-one:

A solution of cyanoacetamide (107 mg, 1.27 mmol) in DMF (3 mL) was added to a stirred suspension of sodium hydride (55.2 mg, 2.3 mmol) in DMF under an atmosphere of nitrogen. To this mixture was added a solution of 6-[1'-N,N-dimethylamino-3'-oxobuten-2'-yl]-3,4-dihydro-1,3-dimethylpyrido[2,3-d]pyrimidin-2(1H)-one (333 mg, 1.15 mmol) in DMF (6 mL). This mixture was heated to 80 degrees C. for 5.5 hours., cooled to room temperature and treated with saturated aqueous $NH_4^+Cl^-$ (10 mL). This mixture was extracted with dichloromethane (3×50 mL), dried over $Na_2SO_4$ and concentrated in vacuo to leave an orange solid, which was purified by column chromatography ($SiO_2$, $CH_2Cl_2$:$CH_3OH$, 90:10) to leave after drying in vacuo (45 degrees C., 60 hours) 140 mg of 6-[3'cyano-6'-methyl-2'-oxo-(1H)pyridin-5'-yl]-3,4- dihydro-1,3-dimethlpyrido-[2,3-d]pyrimidin-2(1H)-one as a pale yellow powder (mp>300 degrees C.)

Analysis (1.4 hydrate): Calculated %C, 57.44; H, 4.94; N, 20.93; Found %C, 57.29; H, 5.04; N,21.05; %C, 57.58; H, 4,92; N, 20.64.

EXAMPLE 3

Preparation of 6-[6'-methyl-2'-oxo-(1H)pyrimidin-4'-yl]-3,4-dihydro-1-methylpyrido[2,3-d]pyrimidin-2(1H)-one:

Treatment of 6-(trimethylstannyl)-1-methyl-3-acetylpyrido[2,3-d]pyrimindin-2(1H)-one with methylmalonoyl in the presence of a small amount of a palladium catalyst such as $PdCl_2(PPh_3)_2$ in an anhydrous solvent such as toluene or tetrahydrofuran at temperatures between 40 and 60 degrees C. for between 1 and 10 hours will afford 6-[1'-(2'-carbomethoxy-1 '-oxyethyl)]-3,4-dihydro-1-methyl-3-acetylpyrido[2,3-d]pyrimidin-2(1H)-one. Treatment of this material with base such as sodium bicarbonate in methanol will afford 6-[1'-(2'-carbomethoxy-1'-oxyethy10]-3,4-dihydro-1-methylpyrido[2,3-d]pyrimidin-2(1H)-one. When treated with acetamidine in a suitable solvent such as ethanol at temperatures between 50 and 150 degrees C. will produce 6- [6'-methyl-2'-oxo-(1H)pyrimidin-4'-yl]-3,4-dihydro-1-methylpyrido[2,3-d]pyrimidin-2(1H)-one.

EXAMPLE 4

Preparation of 6-[2',6'-dioxo-(1H,5H)pyrimidin-4'-yl]-3,4-dihydro-1-methylpyrido[2,3-d]pyrimidin-2(1H)-one:

Treatment of 6-[1'-(2'-carbomethoxy-1'-oxyethyl)]-3,4-dihydro-1-methylpyrido[2,3-d]pyrimidin-2(1H)-one with urea in a suitable solvent such as ethanol at temperatures between 50 and 130 degrees C. will afford 6-[2',6'-dioxo-(1H,5H)pyrimidin-4'-yl]-3,4-dihydro-1-methylpyrido[2,3-d]pyrimidin-2(1H)-one.

EXAMPLE 5

Preparation of 6-[6'-(4,5'-dihydro-3(2H)-3-oxopyridazinyl)]-3,4-dihydro3-methylpyrido[3,2-d]-pyrimidin-2(1H)-one:

Treatment of 2-(methylamino)methyl-3-aminopyridine with a brominating agent such as N-bromosuccinimide will afford 2-(methylamino)methyl-3-amino-6-bromopyridine. Treatment of this material with phosgene or 1,1'-carbonyldiimidazole will afford 6-bromo-3,4-dihydro-3-methylpyrido[3,2-d]pyrimidin-2(1H)-one. Treatment with an alkyllithium reagent such as tert-butyllithium followed by the addition of trimethylstannyl chloride will yield 6-trimethylstannyl-3,4-dihydro-3-methylpyrido[3,2-d]pyrimidin-2(1H)-one. Treatment of this material is treated with carbomethoxypropionyl chloride in the presence of a palladium catalyst such as $PdCl_2(PPh_3)_2$ in an anhydrous solvent such as benzene or tetrahydrofuran at temperatures between 50 and 120 degrees C. will afford 6-[1'-(3'-carbomethoxy-1'-oxypropyl)]-3,4-dihydro-3-methylpyrido[3,2-d]pyrimidin-2(1H)-one, which when treated with hydrazine in a suitable solvent, such as ethanol, will afford 6-[6'-(4',5'-dihydro-3(2H)-3-oxopyridazinyl)]-3,4-dihydro-3-methylpyrido[3,2-d]pyrimidin-2(1H)-one.

EXAMPLE 6

Preparation of 6-[6'-(4',5'-dihydro-3(2H)-3-oxopyridazinyl)]-1,3-dimethylpyrido[2,3-d]pyrimidin-2,4-(1H,3H)-dione:

Treatment of 2-(methylamino) micotinamide with a carbonylating agent such as phosgene or 1,1-carbonyldiimidazole will afford 1-methylpyrido[2,3-d]pyrimidin-2,4-(1H,3H)-dione. Treatment of this material with alkylating agents such as dimethylsulfate or methyliodide in the presence of a base such as sodium bicarbonate or sodium hydroxide will afford 1,3-dimethylpyrido[2,3-d]-pyrimidin-2,4(1H,3H)-dione. Treatment of this material with a brominating agent such as N-bromosuccinimide will afford 6-bromo-1,3-dimethylpyrido[2,3-d]pyrimidin-2,4-(1H,3H)-dione. Treatment with an alkyl lithium reagent such as tert-butyllithium followed by the addition of trimethylstannyl chloride will yield 6-trimethylstannyl-1,3-dimethylpyrido[2,3-d]pyrimidin-2,4(1H,3H)-dione. Treatment of this material with carbomethoxypropionyl chloride in the presence of a palladium catalyst such as $PdCl_2(PPh_3)_2$ in an anhydrous solvent such as benene or tetrahydrofuran at temperatures between 50 and 120 degrees C. will afford 6-[1'-(3'-carbomethoxy-1'-oxypropyl)]-1,3-dimethylpyrido[2,3-d]pyrimidin-2,4-(1H,3H)-dione, which when treated with hydrazine in a suitable solvent, such as ethanol, will afford 6-[6'-(4',5'dihydro-3(2H)-3-oxopyridazinyl)]-1,3-dimethylpyrido[2,3-d]pyrimidin-2,4-(1H,3H)-dione.

EXAMPLE 7

Preparaton of 6-[3'-cyano-6'-methyl-2-oxo(1H)-pyridin-5'-yl)]-1,3 -dimethyl-2H-imidazo[4,5-b]-pyridin-2-one:

Treatment of 1,3-dimethyl-2H-imidazo[4,5-b]pyridin-2-one with a brominating agent such as N-bromosuccimimide will afford 6-bromo-1,3-dimethyl-2H-imidazo[4,5-b]-pyridin-2-one. Treatment of this material with trimethylstannyl acetone in the presence of palladium catalyst such as palladium (II) acetate and a triarylphosphine such as tri-o-tolyl-phosphine in an anhydrous solvent such as benzene at temperatures between 50 and 120 degrees C. will afford 6-(2'oxypropyl)-1,3-dimethyl-2H-imidazo-[4,5-b]-pyridin-2-one. Treatment of this material with N,N-dimethylformamide dimethylacetal in the presence of a catalytic amount of pyridine will afford 6-[1',N,N-dimethylamino-3'-oxobuten-2'-yl]-1,3-dimethyl-2H-imidazo[4,5-b]pyridin-2-one. Treatment of this material with cyanoacetamide in the presence of a base such as sodium hydride in a suitable solvent at temperatures between 30 degrees and 80 degrees C. will afford 6-[3'-cyano-6'-methyl-2'-oxo-(1H)pyridin-5'-yl]-1,3-dimethyl-2H-imidazo[4,5-b]pyridin-2-one.

EXAMPLE 8

Preparation of 6-[3'-cyano-6'-methyl-2'-oxo-(1H)pyridin-5'-yl]-3,4-dihydro-1,3-dimethylpyrido[2,3-d]pyrimidin-2(1H)-one:

Treatment of 6-bromo-3,4-dihydro-3-methylpyrido[3,2-d ]pyrimidin-2(1H)-one with a methylating agent such as methyliodide or dimethylsulfate in the presence of a base such as lithium hexamethyldisilane in an anhydrous solvent such as tetrahydrofuran will afford 6-bromo-3,4-dihydro-1,3-dimethylpyrido[3,2-d]pyrimidin-2(1H)-one. Treatment of this material with trimethylstannyl acetone in the presence of a palladium catalyst such as palladium (II) acetate and a triarylphosphine such as tri-o-tolylphosphine in an anhydrous solvent such as benzene at temperatures between 50 and 120 degrees C. will afford 6-(2'-oxopropyl)-3,4-dihydro-1,3-dimethylpyrido[3,2-d]pyrimidin-2(1H)-one. Treatment of this material with N,N-dimethylformamide dimethylacetal in the presence of a catalytic amount of pyridine will afford 6-[1'-N,N-dimethylamino-3'-oxobuten-2'-yl]-3,4-dihydro-1,3-dimethylpyrido[3,2-d]pyrimidin(1H)-one. Treatment of this material with cyanoacetamide in the presence of a base such as sodium hydride in a suitable solvent at temperatures between 30 degrees and 80 degrees C. will afford 6-[3'-cyano-6'-methyl-2'-oxo-(1H)-pyridin-5'-yl]-3,4-dihydro-1,3-dimethylpyrido[2,3-d]pyrimidin-2(1H)-one.

EXAMPLE 9

Preparation of 6 -[3'-methyl-2'-oxo-(1H)-pyridin-5'-yl]-1,3-dimethylpyrido[2,3-d]pyrimidin-2,4-(1H,3H)-dione:

Treatment of 6-bromo-1,3-dimethylpyrido[2,3-d]pyrimidin-2,4-(1H,3H)-dione with trimethylstannyl acetone in the presence of a palladium catalyst such as palladium (II) acetate and a triarylphosphine such as tri-o-tolylphosphine in an anhydrous solvent such as benzene at temperatures between 50 degrees and 120 degrees C. will afford 6-(2'-oxoproply)-1,3-dimethylpyrido[2,3-d]pyrimidin-2,4-(1H,3H)-dione. Treatment of this material with N,N-dimethylformamide dimethylacetal in the presence of a catalytic amount of pyridine will afford 6-[1-N,N-dimethylamino-3'-oxobuten-2'-yl]-1,3-dimethylpyrido[2,3-d]pyrimidin-2,4-(1H,3H)-dione. Treatment of this material with cyanoacetamide in the presence of a base such as sodium hydride in a suitable solvent at temperatures between 30 degrees and 80 degrees C. will afford 6-[3'-cyano-6'-methyl-2'-oxo-1(H)pyridin-5'-yl]1,3-dimethylpyrido[2,3-d]pyrimidin-2,4-(1H,3H)-dione.

EXAMPLE 10

Preparation of 6'-[3'-cyano-6'-methyl-2'-oxo-(1H)pyridin-5'-yl]-3,4-dihydro-1,3-dimethylpyrido[3,4-d]-pyrimidin-2(1H)-one:

Treatment of 3-amino-6-bromo-4-pyridinecarboxamide with a reducing agent such as diborane will afford 3-amino-4-aminomethyl-6-bromopyridine. Treatment of this material with a carbonylating agent such as phosgene or N,N'-carbonyldiimidazole in an anhydrous, aprotic solvent such as tetrahydrofuran or toluene at temperatures between 25 degrees and 100 degrees C. will afford 6-bromo-3,4-dihydropyrido[3,4-d]pyrimidin-2(1H)-one. Treatment of this material with at least two mole equivalents of a methylating agent such as methyliodide or dimethlsulfate in the presence of a suitable base such as sodium hydride or potassium hydroxide in an inert solvent will afford 6'-bromo-1,3-dimethyl-3,4-dihydropyrido[3,4-d]pyrimidin-2(1H)-one. Treatment of this material with tributylstannylacetone in the presence of a palladium catalyst such as palladium (II) acetate and a triarylphosphine such as tri-o-tolylphosphine in an inert solvent such as toluene at temperatures between 30 degrees and 120 degrees will afford 6-(2'-oxypropyl)-1,3-dimethyl-3,4-dihydropyrido[3,4-d]pyrimidin-2(1H)-one. Treatment of this material with N,N-dimethylformamide dimethylacetal in the presence of a catalytic amount of pyridine will afford 6-[1'-N,N-dimethylamino-3'-oxobuten-2'-yl]-1,3-dimethyl-3,4-dihydropyrido[3,4-dipyrimidin-2(1H)-one. Treatment of this material with cyanoacetamide in the presence of a base such as sodium hydride or potassium tert-butoxide in a suitable solvent at temperatures between 30 degrees and 80 degrees C. will afford 6'-[3'-cyano-6'-methyl-2'-oxo-(1H)pyridin-5'-yl]3,4-dihydro-1,3-dimethylpyrido[3,4-d]pyrimidin-2(1H)-one.

EXAMPLE 11

Preparation of 6-[3'-cyano-6'-methyl-2'-oxo'(1H)-pyridin-5'-yl]-3,4-dihydro-1,3-dimethylpteridin-2(1H)-one:

Treatment of 6-bromo-3-amino-2-pyrazinecarboxamide with a reducing agent such as diborane will afford 6-bromo-3-amino-2-pyrazinemethaneamine. Treatment of this material with a carbonylating agent such as phosgene or N,N'-carbonyldiimidazole in an anhydrous, aprotic solvent such as tetrahydrofuran or toluene at temperatures between 25 degrees and 100 degrees C. will afford 6-bromo-3,4-dihydropteridin-2(1H)-one. Treatment of this material with at least two mole equivalents of a methylating agent such as methyliodide or dimethylsulfate in the presence of a suitable base such as sodium hydride or potassium hydroxide in an inert solvent will afford 6-bromo-1,3-dimethyl-3,4-dihydropteridin-2(1H)-one. Treatment of this material with tributylstannyl acetone in the presence of a palladium catalyst such as palladium (II) acetate and a triaryl phosphine such as tri-o-tolyphosphine in an inert solvent such as toluene at temperatures between 30 degrees and 120 degrees C. will afford 6-(2'-oxyproply)-1,3-dimethyl-3,4-dihydropteridin2(1H)-one. Treatment of this material with cyanoacetamide in the presence of a base such as sodium hydride or potassium tert-butoxide in a suitable solvent at temperatures between 30 degrees and 80 degrees C. will afford 6-[3'-cyano-6'-methyl-2'-oxo-(1H)pyridin-5'-yl]-3,4-dihydro-1,3-dimethylpteridin-2(1H)-one.

EXAMPLE 12

Preparation of 6-[3'-cyano-6'-methyl-2'-oxo-(1H)pyridin-5'-yl-3,4-dihydro-1,3-dimethylpyrimido[5,4-d]pyrimidin-2(1H)-one:

Treatment of 2-bromo-5-amino-4-pyrimidinecarboxamide with a reducing agent such as diborane will afford 2-bromo- 5-amino-4-pyrimidinemethaneamine. Treatment of this material with a carbonylating agent such as phosgene or N,N'-carbonyldiimidazole in an anhydrous, aprotic solvent such as tetrahydrofuran or toluene at temperatures between 25 degrees and 100 degrees C. will afford 6-bromo-3,4-dihydropyrimido[5,4-d]pyrimidin2(1H)-one. Treatment of this material with at least two mole equivalents of a methylating agent such as methyl iodide or dimethyl sulfate in the presence of a suitable base such as sodium hydride or potassium hydroxide in an inert solvent will afford 6-bromo-1,3-dimethyl-3,4-dihydropyrimio[5,4-d]pyrimidin-2(1H)-one. Treatment of this material tributylstannyl acetone in the presence of a palladium catalyst wuch as palladium (II) acetate and a triarylphosphine such as tri-o-tolylphosphine in an inert solvent such as toluene at temperatures between 30 degrees and 120 degrees C. will afford 6-(2'-oxypropyl)-1,3-dimethyl-3,4-dihydropyrimido[5,4-d]pyrimidin-2(1H)-one. Treatment of this material with N,N-dimethylformamide dimethylacetal in the presence of a catalytic amount of pyridine will afford 6-[1'N-N-,-dimethylamino-3'-oxo-buten-2'-yl]-1,3-dimethyl-3,4-dihydropyrimido[5,4-d]pyrimidin-2(1H)-one. Treatment of this material with cyanoacetamide in the presence of a base such as sodium hydride or potassium tert-butoxide in a suitable solvent at temperatures between 30 degrees and 80 degrees will afford 6-[3'-cyano-6'-methyl-2'-oxo-(1H)-pyridin-5'-yl]-3,4-dihydro-1,3-dimethylpyrimido[5,4-d]pyrimidin-2(1H)-one.

The compounds of invention possess positive inotropic activity and are useful as cardiotonic agents in the treatment of humans and other animals, particularly other mammals for cardiac disorders including congestive heart failure. The effectiveness of the compounds of this invention as inotropic agents may be determined by the following pharmacologic tests which evaluate the change in cardiac contractile force upon exposure to a dose of said compounds. The anesthetized dog procedure is a standard test procedure; the inotropic results of this procedure generally correlate with the inotropic activity found in human patients.

Ganglionic-Beta Blocked Anesthetized Dog Procedure

Adult mongrel dogs of either sex weighing 10 to 16 kg are fasted overnight, anesthetized with pentobarbital sodium 35 mg/kg, i.v. intubated, respired with room air using a Harvard respirator, and instrumented surgically to monitor myocardial contractile force, heart rate, arterial pressure, aortic flow and EKG limb lead II. The aforesaid measurements are recorded continuously on a strip chart recorder.

Myocardial contractile force is monitored by a Walton-Brodie strain gauge sutured to the left ventricular myocardium parallel to the left anterior descending coronary artery. Arterial pressure is measured using a fluid-filled catheter attached to a pressure transducer introduced via the right femoral artery and positioned in the thoracic aorta. Mean arterial pressure is determined by electronically clamping the pulsatile pressure signal. Aortic flow is monitored using a precalibrated, noncannulating electromagnetic flow probe positioned around the thoracic aorta. Heart rate is monitored using a cardiotachometer triggered by the QRS complex of the limb lead II EKG. The right femoral vein is cannulated for intravenous infusion of drugs. Body temperature is maintained at $37 \pm 1$ degree C.

Following a 30 min postsurgical stabilization period, control values are recorded. Myocardial depression is induced by ganglionic and beta receptor blockade. Initially, the responsiveness of the autonomic nervous system is assessed by performing a 30 sec bilateral carotid occlusion (BCO). Ten minutes later, a saline solution of isoproterenol 0.3 mcg/kg i.v. is administered to assess beta receptor integrity. Ten minutes after that, a saline solution of mecamylamine 2 mg/kg i.v. is infused, followed by a saline solution of propranolol 1 mg/kg i.v. plus 0.3 mg/kg/hr. Twenty five minutes later, a second BCO is performed to demonstrate ganglionic blockade followed by a send injection of saline isoproterenol 0.3 mcg/kg i.v. to demonstrate beta blockade. Ten minute later, the test compound or vehicle is administered intravenously in ascending doses at 30 min intervals at 1.5 ml/ml in a total volume of 3.5 ml. On completion of the experiment, both BCO and isoproterenol challenges are repeated to verify ganglionic and beta blockage.

The results of the blocked dog test show that compounds of the present invention increase contractile force and aortic blood flow in a dose-related manner while maintaining arterial pressure and having minimal effects on heart rate.

Additional test procedures which have been found to be an efficient means for ascertaining the inotropic activity of the compounds of this invention are described below.

The following test procedure is a standard test for determining the oral activity of the present compounds.

Conscious Instrumented Dog

Mongrel dogs (10-18.5 kg) are anesthetized with sodium pentobarbital (35 mg/kg i.v., supplemented as necessary during surgery) intubated and connected to a Harvard respirator. The left side of the chest is opened at the fith intercostal space, and a Konigsberg transducer inserted into the left ventricle through a puncture at the apex and secured. A fluid-filled polyethylene catheter is inserted into the left atrium through a puncture wound and secured for measurement of left atrial pressure. A second fluid-filled catheter is inserted into the aorta for measurement of blood pressure and heart rate and secured to the vessel wall. The two catheters and the Konigsberg transducer cable are passed out of the chest through the seventh intercostal space and advanced subcutaneously to the back of the neck and passed through the skin. The fluid-filled catheters are filled with heparinized 50% dextrose solution, and the chest is closed and evacuated.

The dogs are treated daily post-operatively with 600,000 units of penicillin-procaine i.m. for ten days and with chloramphenicol, 500 mg/kg i.m., every other day for 10 days and allowed at least 7 days recovery before use.

Each dog is trained and acclimated to her environment and the presence of personnel during the experiment.

The following in vitro method is another means for measuring the inotropic potency of the present compounds. is method is a modification of the enzyme inhibition method reported by Thompson, W. J. and Appleman, M. M., "Characterization of Cyclic Nucleotide Phosphodiesterase of Rat Tissue," J. Biological Chemistry, Vol. 246, pp. 3145-3150 (1971); and Thompson, W. J., Brooker, G. and Appleman, M. M., "Assay of Cyclic Nucleotide Phosphodiesterase with Radioactive Substrates," Methods in Enzymology Vol. 38, pp. 205-212 (1974); and is believed to correlate to in vitro intropic activity in humans.

Inhibition of Peak III cAMP Phosphodiesterase Activity

The test compounds are included in media comprising a radioactively labeled substrated ($^3$H-cyclic nucleotide) such as adenosine 3':5'-monophosphate (cyclic AMP) and guanosine-3':5'- monophosphate (cyclic GMP), and a non-rate-limiting amount of 5'-nucleotidease isolated from a dog heart. The inhibition of the enzyme hydrolysis of the 5'-nucleotide product of the cNUC-PDEase to the corresponding nucleoside is measured by separating the charged, unhydrolyzed substrate from the uncharged hydrolysis product. Separation may be achieved either chromatrographically from the uncharged nucleoside product of the assay with ion-exchange resin or preferentially quenched with the ion-exchange resin so that it is not quantitated with the liquid scintillation counter.

Compounds of the present invention possess peak III phosphodiesterase inhibiting activity.

What is claimed is:
1. A compound having the structure:

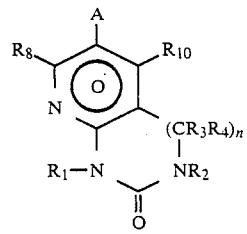

or a pharmaceutically acceptable salt thereof wherein:
A is

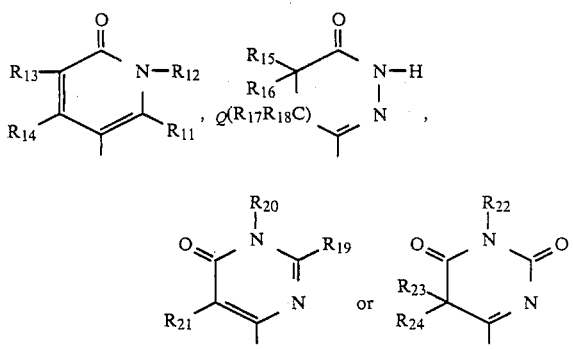

and $R_1$, $R_2$, $R_3$, $R_4$, $R_8$, $R_{10}$, $R_{11}$, $R_{12}$, $R_{14}$, $R_{15}$, $R_{16}$, $R_{17}$, $R_{18}$, $R_{19}$, $R_{20}$, $R_{21}$, $R_{22}$, $R_{23}$ and $R_{24}$ are H, lower alkyl of 1-4 carbon atoms or substituted phenyl lower alkyl of 1-4 carbon atoms;

wherein the substituted phenyl group is substituted by one or more of lower alkyl, lower alkoxy, amino, lower alkyl amino, lower alkyl mercapto, hydroxy, hydroxy lower alkyl, acetoxy, benzyloxy, phenoxy, lower alkyl sulfinyl or lower alkyl sulfonyl;

$R_{13}$ is H, lower alkyl of 1-4 carbon atoms, alkoxy lower alkyl of 1-4 carbon atoms, hydroxy lower alkyl of 1-5 carbon atoms, amino, carbamoyl, cyano, lower allkyl carbamoyl of 1-4 carbon atoms, formyl, amino lower alkyl of 1-4 carbon atoms, carboxy, carbalkoxy, or tetrazolyl;

$R_3$ and $R_4$ together may form =O;

$R_{16}$ and $R_{17}$ together may form a carbon-carbon bond;

n is 0 or 1; and

Q is 0 or 1.

2. A method for increasing cardiac contractility in a human or other animal requiring such treatment which comprises administering thereto an effective inotropic amount of a compound according to claim 1.

3. A pharmaceutical composition for increasing cardiac contractility in a human or other animal requiring such treatment comprising an effective inotropic amount of a compound according to claim 1 in admixture with a pharmaceutically acceptable carrier.

4. A compound of claim 1 wherein
$R_8$ and $R_{10}$ are hydrogen;
$R_3$ and $R_4$ are each hydrogen or together form =O.

5. A compound of claim 4 wherein A is:

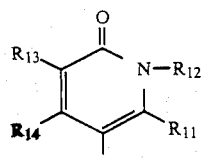

6. A compound of claim 4 wherein A is

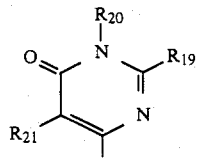

7. A compound of claim 4 wherein A is:

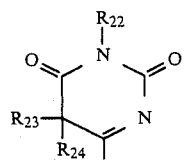

8. A compound according to the structure:

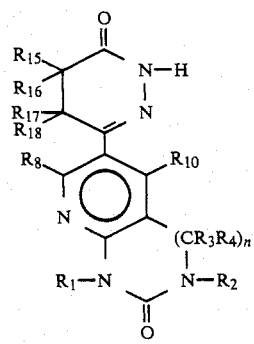

or a pharmaceutically acceptable salt thereof, wherein
n is 0 or 1;
$R_1$ is H or lower alkyl of 1-4 carbon atoms;
$R_2$ is H or lower alkyl of 1-4 carbon atoms;
$R_3$ is H or lower alkyl of 1-4 carbon atoms;
$R_4$ is H or lower alkyl of 1-4 carbon atoms;
$R_8$ is H or lower alkyl of 1-4 carbon atoms;
$R_{10}$ is H or lower alkyl of 1-4 carbon atoms;
$R_{15}$ is H or lower alkyl of 1-4 carbon atoms;
$R_{16}$ is H or lower alkyl of 1-4 carbon atoms;
$R_{17}$ is H or lower alkyl of 1-4 carbon atoms;
$R_{16}$ and $R_{17}$ may together form a carbon-carbon double bond; and
$R_{18}$ is H or lower alkyl of 1-4 carbon atoms.

9. A compound according to the structure:

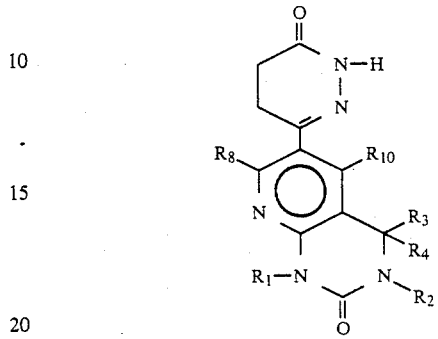

or a pharmaceutically acceptable salt thereof, wherein
$R_1$ is H or methyl;
$R_2$ is H or methyl;
$R_3$ is H;
$R_4$ is H, methyl, or together with $R_3$ forms =O;
$R_8$ is H, or methyl; and
$R_{10}$ is H, or methyl.

10. A compound of claim 9 being 6-[6'-(4',5'-Dihydro-3(2H)-3-pyridazinyl)]-3,4-dihydro-1-methyl-pyrido-[2,3-d]pyrimidin-2-(1H)-one.

11. A compound of claim 5 being 6-[3'-Cyano-6'-methyl-2'-oxo-(1H)pyridin-5'-yl]-3,4-dihydro-1,3-dimethylpyrido[2,3-d]pyrimidin-2(1H)-one.

12. A compound of claim 6 being 6-[6'-Methyl-2'-oxo-(1H)pyrimidin-4'-yl]-3,4-dihydro-1-methyl-pyrido[2,3-d]pyrimidin-2(1H)-one.

13. A compound of claim 7 being 6-[2',6'-Dioxo-(1H,5H)pyrimidin-4'-yl]-3,4-dihydro-1-methyl-pyrido[2,3-d]pyrimidin-2(1H)-one.

14. A compound of claim 1 being 6-[3'-cyano-6'-methyl-2'-oxo-(1H)pyridin-5'-yl]-3,4-dihydro-1,3-dimethylpyrido[3,4-d]pyrimidin-2(1H)-one.

15. A compound of claim 9 being 6[6'-(4',5'-Dihydro-3(2H)-3-oxo-pyridazinyl)]1,3-dimethylpyrido[2,3-d]pyrimidin-2,4-(1H,3H)-dione.

16. A compound of claim 1 being 6-[3'-Cyano-6'-methyl-2'-oxo-(1H)pyridin-5'-yl]-1,3-dimethyl-2H-imidazo[4,5-b]pyrindin-2-one.

17. A compound of claim 5 being 6-[3'-Cyano-6'-methyl-2'-oxo-(1H)pyridin-5'-yl]-1,3-dimethylpyridio[2,3-d]pyrimidin-2,4-(1H,3H)-dione.

* * * * *